United States Patent [19]

Wood

[11] 4,082,812
[45] Apr. 4, 1978

[54] CHLORINATED CYCLOPENTADIENE PEROXIDES

[75] Inventor: Donald W. Wood, San Pablo, Calif.

[73] Assignee: Argus Chemical Corporation, Brooklyn, N.Y.

[21] Appl. No.: 790,521

[22] Filed: Apr. 25, 1977

[51] Int. Cl.² .................. C07C 179/08; A01N 9/24
[52] U.S. Cl. .......................... 260/610 R; 424/338
[58] Field of Search ........... 260/610 R, 610 B, 610 C, 260/610 A; 424/338

[56] References Cited

U.S. PATENT DOCUMENTS 2,501,967   3/1950   Vaughan et al. ............... 260/610 R

*Primary Examiner*—James O. Thomas, Jr.
*Assistant Examiner*—W. B. Lone
*Attorney, Agent, or Firm*—Townsend and Townsend

[57] ABSTRACT

An organic peroxide of the formula

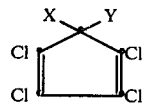

wherein X and Y are both selected from the same one of the following two subparagraphs:
(a) each of X and Y is the same and is a peroxy alkyl group of the structure —OOR in which R is a t-alkyl group of 4–8 carbon atoms;
(b) X is chlorine and Y has the structure

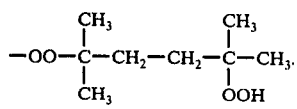

5 Claims, No Drawings

CHLORINATED CYCLOPENTADIENE PEROXIDES

This invention relates to organic peroxide polymerization initiators. More particularly, it relates to organic peroxides made from hexachlorocyclopentadiene.

Previously hexachlorocyclopentadiene has been used as a reactant in the formation of ketals. In the present invention this same starting reactant is used for the preparation of a series of organic peroxides. As a group that new peroxides of this invention have the formula:

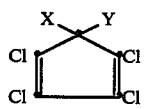

wherein X and Y are both selected from the same one of the following two subparagraphs:
 (a) each of X and Y is the same and is a peroxy alkyl group of the structure —OOR in which R is a t-alkyl group of 4-8 carbon atoms;
 (b) X is chlorine and Y has the structure

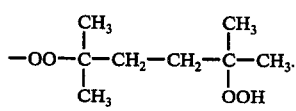

In connection with those molecules in which X and Y are of the structure -OOR, R is a tertiary alkyl group as indicated. The alkyl substituents on the tertiary carbon atom may be straight or branched chain. Thus, structures such as the 1,1,3,3-tetramethyl butyl group are contemplated for R, as well as t-alkyl groups having straight chain substituents on the tertiary carbon atom.

The novel peroxides of this invention have utility as initiators for the curing of unsaturated polyester resins. They are also useful as polymerization initiators of styrene, methyl methacrylate and ethylene. Besides being advantageous polymerization initiators, additional benefits accrue from the high chlorine content of the molecules which tend to impart fire retardant qualities to the polymer products. In addition, the polychlorinated pentadiene structure is believed to have biological activity analogous to the properties of various insecticides, germicides and fungicides made from hexachlorocyclopentadiene.

The new molecules may be formed in accordance with the following general reaction schemes.

(a) Where X and Y are both peroxy alkyl groups the following reaction is used:

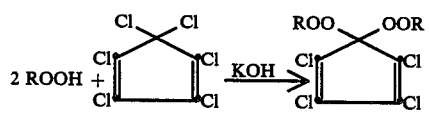

(b) For reaction with 2,5-dimethyl-2,5-dihydroperoxy hexane the reaction used is:

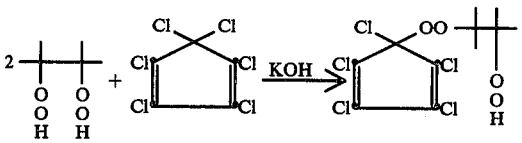

The following examples will illustrate the preparation and utility of the novel peroxides. In the synthesis work the usual methods for determining active oxygen (AO) could not be utilized because the presence of double bonds and chlorine atoms in the peroxides interfere with the usual iodometric assay methods.

EXAMPLE I

Synthesis of 1,1-bis(t-butyl peroxy)tetrachlorocyclopentadiene 28.8 g. of 69% aqueous t-butyl hydroperoxide (TBHP) (0.22 moles) and 24.7 g. of 50% KOH (0.22 mole) were added to about 90 g. of ice in an 8 oz. bottle. Then 13.64 g. of hexachlorocyclopentadiene (0.05 mole) and 0.88 g. trioctyl propyl ammonium chloride (phase transfer catalyst) were added to the contents in the bottle. It was capped and placed on a shaker. After 10 minutes, the bottle became warm to the touch and was cooled in an ice bath. When cooled, the bottle was replaced on the shaker for a total of 22 hours.

The organic phase was separated and concentrated under vacuum and yielded 13.44 g. of a crude liquid product (70.7% yield). This crude reaction product is utilized in the experimental work reported in Table 1.

The crude product was purified by column chromatography using silica gel and petroleum ether. Infrared (IR) analysis of purified product shows C-H bonds. The purified product had a specific gravity (25° C.) of 1.405 and a refractive index, $\eta_D^{25}$, of 1.517.

Analyses of the aqueous layer recovered from the reaction and the material from the cold trap indicate that 2.3 moles of TBHP/mole hexachlorocyclopentadiene were consumed (2.0 theory), and 2.2 moles of ionic chloride/mole hexachlorocyclopentadiene were released (2.0 theory). This purified product was utilized in the experimental results shown in Table 2.

EXAMPLE II

Synthesis of 1,1-bis(t-amyl peroxy)tetrachlorocyclopentadiene

This peroxide was prepared in a similar manner to Example I by substituting t-amyl hydroperoxide for the TBHP. 10.03 g. of purified liquid product was isolated from the column chromatography step (20.41 g. theory, 49.1% yield). The purified product had a specific gravity (25° C.) of 1.401 and a refractive index, $\eta_D^{25}$, of 1.517. Thin layer chromatography (TLC) on alumina indicates one major component which is not hexachlorocyclopentadiene. This purified product was utilized in the experimental results shown in Table 2.

EXAMPLE III

Reaction Product from hexachlorocyclopentadiene with 2,5-dimethyl-2,5-dihydroperoxy hexane 13.64 g. hexachlorocyclopentadiene (0.05 mole) and 25.43 g. of 77.08% 2,5-dimethyl-2,5-dihydroperoxyhexane (0.11 mole) were reacted in a similar manner to Example I using 60 g. of dichloromethane as a solvent.

The organic phase was separated, concentrated under vacuum, and washed with caustic to remove unreacted dihydroperoxide. Crude product yield was 15.38 g. (74.2% of theory). This crude reaction product was used as a polyester curing agent with results shown in Table 3 under Peroxide #2.

This product was then purified by column chromatography using silica gel and ether. The purified product was a thick, viscous amber liquid weighing 9.17 g. (44.2% of theory). TLC on alumina indicates one major component which is neither hexachlorocyclopentadiene nor 2,5-dimethyl-2,5-dihydroperoxy hexane. IR analysis shows the presence of —OOH bond. Analysis of the aqueous layer recovered from the reaction indicates that only 1.55 mole of ionic chloride/mole hexachlorocyclopentadiene was released. Based upon the evidence, the product is believed to be:

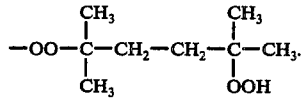

This purified product was used as a polyester curing agent with the results shown in Table 3 under Peroxide #3.

Table 1
Hot Block Gel Tests with Various Peroxides

Comparison of Various Samples of 1,1-bis(t-Butyl peroxy) Tetrachklorocyclopentadiene in Hatco GR-941 Unsaturated Polyester Resin at 275° F.

| Peroxide | Time, Min. for 0 to 85° F. | 0 to Peak | Peak Exotherm, ° F. |
|---|---|---|---|
| 1. 1.0% 1,1-Bix(t-butyl peroxy) Cyclohexane | 1.21 | 1.60 | 368.2 |
| 2. 1.0% Hexachloro Cyclopentadiene | No gel after 13 minutes | | |
| 3. 1.0% Crude 1,1-bis(t-butyl peroxy) tetrachloro cyclopentadiene, Run 1 | 1.33 | 1.97 | 355.7 |
| 4. 2.0% same as peroxide #3 above | 1.26 | 1.83 | 356.5 |
| 5. 1.0% Crude 1,1-bis(t-butyl peroxy) tetrachloro cyclopentadiene, Run 2 | 1.22 | 1.75 | 369.7 |
| 6. 1.0% Crude 1,1-bis(t-butyl peroxy) tetrachloro cyclopentadiene, Run 3 | 1.16 | 1.68 | 359.0 |

Table 2
Hot Block Gel Tests with Various Peroxides

Comparison of Various Peroxides Made from Hexachlorocyclopentadiene with Other Peroxides in Hatco GR-941 Unsaturated Polyester Resin at 260° F.

| Peroxide | Gel Time, Min. | Extherm Time, Min. | Peak Exotherm, ° F. |
|---|---|---|---|
| 1. 1.0% t-Butyl Peroxybenzoate | (a) 2.13 | 2.63 | 379 |
| | (b) 2.11 | 2.66 | 377 |
| 2. 1.0% 1,1-bis(t-butyl peroxy) Cyclohexane | (a) 1.37 | 1.91 | 342 |
| | (b) 1.30 | 1.86 | 338 |
| 3. 1.0% 1,1-bis(t-amyl peroxy) Cyclohexane | (a) 1.22 | 1.70 | 343 |
| | (b) 1.22 | 1.69 | 333 |
| 4. 1.0% purified 1,1-bis(t-butyl peroxy) Tetrachlorocyclopentadiene | (a) 1.21 | 1.70 | 348 |
| | (b) 1.23 | 1.76 | 350 |
| 5. 0.75% purified 1,1-bis(t-amyl peroxy) Tetrachlorocyclopentadiene | (a) 1.31 | 1.92 | 344 |
| | (b) 1.33 | 1.86 | 343 |
| 6. 1.0% same as peroxide #5 above | (a) 1.31 | 1.84 | 336 |
| | (b) 1.34 | 1.87 | 335 |

Table 3
Hot Block Gel Tests with Various Peroxides

Comparison of Peroxide Made from Hexachlorocyclopentadiene and 2,5-Dimethyl-2,5-Dihydroperoxy Hexane with t-Butyl Peroxybenzoate in Hatco GR-941 Unsaturated Polyester Resin at 270° F.

| Peroxide | Gel Time, Min. | Exotherm Time, Min. | Peak Exotherm, ° F. |
|---|---|---|---|
| 1. 1.0% t-ButylPeroxybenzoate | 1.74 | 2.24 | 379.5 |
| 2. 1.0% Crude product from reaction of Hexachlorocyclopentadiene with 2,4-Dimethyl-2,5-Dihydroperoxy hexane | 1.42 | 2.16 | 352.2 |
| 3. 1.0% purified, same as peroxide #2 above | 1.24 | 1.80 | 358.5 |

I claim:
1. An organic peroxide of the formula

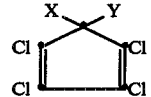

wherein X and Y are both selected from the same one of the following two subparagraphs:
(a) each of X and Y is the same and is a peroxy alkyl group of the structure —OOR in which R is a t-alkyl group of 4–8 carbon atoms;
(b) X is chlorine and Y has the structure $$-OO-\underset{\underset{CH_3}{|}}{\overset{\overset{CH_3}{|}}{C}}-CH_2-CH_2-\underset{\underset{OOH}{|}}{\overset{\overset{CH_3}{|}}{C}}-CH_3.$$

2. An organic peroxide in accordance with claim 1 wherein each of X and Y is a peroxy alkyl group of the same structure —OOR in which R is a t-alkyl group of 4-8 carbon atoms.

3. An organic peroxide in accordance with claim 1 wherein X is chlorine and Y has the structure $$-OO-\underset{\underset{CH_3}{|}}{\overset{\overset{CH_3}{|}}{C}}-CH_2-CH_2-\underset{\underset{OOH}{|}}{\overset{\overset{CH_3}{|}}{C}}-CH_3.$$

4. An organic peroxide in accordance with claim 2 wherein R is a t-butyl group.

5. An organic peroxide in accordance with claim 2 wherein R is a t-amyl group.